United States Patent [19]

Geus

[11] Patent Number: 5,787,145
[45] Date of Patent: Jul. 28, 1998

[54] METHOD AND ARRANGEMENT FOR IDENTIFYING CRYSTALLINE AND POLYCRYSTALLINE MATERIALS

[75] Inventor: Georg Geus, Wiesbaden, Germany

[73] Assignee: Heimann Systems GmbH, Germany

[21] Appl. No.: 619,410

[22] Filed: Mar. 21, 1996

[30] Foreign Application Priority Data

Mar. 21, 1995 [DE] Germany .................. 195 10 168.5

[51] Int. Cl.⁶ ..................................... G01N 23/20
[52] U.S. Cl. ..................................... 378/71; 378/57
[58] Field of Search ..................... 378/57, 88, 71

[56] References Cited

U.S. PATENT DOCUMENTS

| | | | |
|---|---|---|---|
| 4,956,856 | 9/1990 | Harding | 378/88 |
| 5,007,072 | 4/1991 | Jenkins et al. . | |
| 5,247,561 | 9/1993 | Kotowski | 378/88 |
| 5,263,075 | 11/1993 | McGann et al. . | |
| 5,394,453 | 2/1995 | Harding . | |

FOREIGN PATENT DOCUMENTS

| | | |
|---|---|---|
| 0209952A2 | 1/1987 | European Pat. Off. . |
| 0 354 045 | 2/1990 | European Pat. Off. . |
| 2461877 | 7/1976 | Germany . |
| 3023263C2 | 8/1986 | Germany . |

*Primary Examiner*—Craig E. Church
*Attorney, Agent, or Firm*—Spencer & Frank

[57] ABSTRACT

A method and apparatus is provided for identifying crystalline and polycrystalline material in an object placed in an examination region. X-rays having a polychromatic energy distribution are passed through a diaphragm to create a central x-ray beam in a fan plane that is projected into the examination region for irradiating a cross section of the object. The x-rays are diffracted by individual subregions of the object along the cross section in dependence of the presence of crystalline and/or polycrystalline material in the individual subregions. Collimators with collimating windows are arranged beyond the examination region with respect to the diaphragm, each collimating window covering a fixed, predetermined subregion of the examination region and extracting at least one diffracted plane fan beam from the respective individual subregion of the object. Energy spectra of the diffracted x-ray plane fan beams exiting the respective one of the collimating windows are captured with a detector located behind each of the collimating windows for converting the captured energy spectra into signals usable in a data processing arrangement.

17 Claims, 4 Drawing Sheets

METHOD AND ARRANGEMENT FOR IDENTIFYING CRYSTALLINE AND POLYCRYSTALLINE MATERIALS

CROSS-REFERENCE TO RELATED APPLICATIONS

This application claims priority of German application No. 195 10 168.5, filed in Germany on Mar. 21, 1995, the disclosure of which is incorporated herein by reference.

BACKGROUND OF THE INVENTION the invention relates to a method and arrangement for identifying crystalline and polycrystalline material in an object, and in particular to such a method and arrangement wherein the object is irradiated in an examination region with x-rays having a polychromatic energy distribution, which x-rays are diffracted along a material volume of the object in dependence of the presence of crystalline and polycrystalline material and the energy spectra of the diffracted x-rays are captured in detectors and converted to usable signals in a data processing arrangement.

In order to ensure aviation safety, it is necessary to check passenger baggage by employing the most modern technical resources. In this context, the detection of bombs or plastic explosives contained in baggage is of particular importance since the hazard potential increases from year to year. Inspection or detection arrangements are required to have a low rate of false alarms and a high likelihood of detection while working at high throughput rates. At the same time, such systems are required to portray a high degree of sturdiness and availability. Analysis methods as they are employed in the laboratory can only be applied to a limited extent. In order to meet these demands, multi-stage systems, for example, are used.

It is possible, in principle, to employ the physical effect of x-ray diffraction at lattice planes or crystalline and polycrystalline materials by an appropriate selection of a beam geometry. X-ray diffractometry has been known for many years for identifying and classifying materials, not only on surfaces but also in a transmission process to obtain material information within spatially expanded examination objects, for example, airplane baggage.

In the simplest case, an object is penetrated by an x-ray having a small cross section. If the object is comprised of materials with a crystalline or polycrystalline lattice structure, individual quanta are diffracted at this structure. In general, the diffracted radiation will disappear through destructive interference. But intensifications of these energy emissions occur as well.

This is always the case if an allocated wavelength 1 appears at a specific angle θ to the crystal plane and a structural interference appears at a material-specific spacing d between the crystal planes. The known Bragg interference condition summarizes the relationships between λ, θ and the lattice spacing d as follows:

$$2d \times \sin\theta = n \times \lambda$$

As can be seen from tis relationship, the effect may be applied in different ways. If a polycrystalline material is exposed to a polychromatic x-ray source, different energy maxima appear at an angle θ which, for example, is to be considered as being fixed. These maxima are characteristic for the lattice spacings in the examined material. Studies have shown that, due to their polycrystalline structure, explosive substances generate such energy spectra. Thus, this method is suitable, in principle, for detecting explosive substances. A sought after material is identified by comparing the measured spectrum with a catalog of relevant spectra deposited in a data memory. Such methods are customary, for example, in x-ray diffractometry IR spectroscopy and gas chromatography and they are not explained here in detail.

European patent publication EP-0 209 952 A2 discloses that products which are comprised of different scattering angles and the energies associated therewith are combined in groups and analyzed. In the arrangement disclosed in this publication, cylinder collimators upstream and downstream of the object to be examined result in circular or annular images and corresponding detector geometries. For the examination of the volume regions along the irradiated x-ray bundle, that is in the depth of the object, it is necessary that the object be displaced longitudinally with respect to the incident x-ray and/or that the entire arrangement be subjected to a lateral relative movement with respect to the object to be examined. For this method, a plurality of consecutive measurements is required because only a single point of the cross-sectional plane along the irradiated x-ray bundle can be examined during each measurement. During such point-by-point detection it is necessary that each detector captures the scattered radiation in a plurality of angle positions and displacement positions, which means that a large time and computational expenditure is necessary.

SUMMARY OF THE INVENTION

It is an object of the invention to improve upon the known method and arrangement described above so that a substantial simplification and a more cost-advantageous solution are created which solution allows a time-parallel examination of all volume elements of an object along an incident x-ray.

The above and other objects are accomplished according to the invention by the provision of a method for identifying crystalline and polycrystalline material in an object, comprising: placing the object in an examination region; passing x-rays having a polychromatic energy distribution through a diaphragm to create a central x-ray beam in a fan plane that is projected into the examination region for irradiating a cross section of the object, the x-rays being diffracted by individual subregions of the object along the cross section in dependence of the presence of at least one of crystalline and polycrystalline material in a respective one of the individual subregions; arranging collimators with collimating windows beyond the examination region with respect to the diaphragm, each collimating window covering a fixed, predetermined subregion of the examination region and extracting at least one diffracted plane fan beam from the respective individual subregion of the object, and capturing energy spectra of the diffracted x-ray plane fan beam exiting a respective one of the collimating windows with detectors each located behind a respective one of the collimating widows for converting the captured energy spectra into signals usable in a data processing arrangement.

According to another aspect of the invention there is provided an arrangement for identifying crystalline and polycrystalline material in an object, comprising: an x-ray source including a diaphragm for projecting a central x-ray beam having a polychromatic energy distribution in a fan plane into an examination region containing the object for irradiating a cross section of the object, the x-rays being diffracted by individual subregions of the object along the cross section in dependence of the presence of at least one of crystalline and polycrystalline material in a respective one of the individual subregions; collimators arranged beyond the examination region relative to the x-ray source, the collimators being arranged in at least one row symmetrically around the axis of the central x-ray beam in a plane extending perpendicularly to the fan plane of the central x-ray beam and including collimating windows extending in parallel with respect to one another and respectively at a fixed angle α with respect to the axis of the central x-ray beam, each collimating window covering a fixed, predetermined subregion of the examination region and extracting at least one diffracted plane fan beam from the respective individual subregion of the object; and detectors each arranged at a respective one of the collimating windows of the collimators in the plane of the respectively collimated fan beam for capturing energy spectra of the diffracted x-ray plane fan beam exiting a respective one of the collimating windows and converting the energy spectra into signals for subsequent use in a data processing arrangement.

According to the invention the circular collimation devices used in the known arrangement are replaced by linear collimating devices and substantial improvements are accomplished by conducting a time-parallel examination of all volume elements or subregions of the object along the incident x-ray beam. A simplification is essentially accomplished in that the collimators arranged beyond the examination region extract at least one diffracted, fan beam from the respective subregion and each collimating window of the collimators covers a fixed, predetermined subregion of the cross-sectional plane of the examined object.

The method and the arrangement of the invention allow a simultaneous detection of all of the subregions that are fixedly predetermined in the cross-sectional plane of the object so that a complete cross section of the object can be inspected successively at short time intervals. According to another aspect of the method and arrangement of the invention, a high detection accuracy is achieved because the collimation and detection unit can be oriented automatically toward the focus of the x-ray source and can be adjusted. The collimating and detection unit may be arranged in different planes along the incident x-ray, preferably in a horizontal and vertical plane, so that a faster detection of the material of interest in the examined object is possible by way of multiple measurements of an examination region.

In a further advantageous manner, the method and the arrangement of the invention make possible the use of silicon photodiodes as semiconductor detectors and thus offer a simplification and a more cost-advantageous solution compared to the use of, for example, cooled germanium detectors which are normally required for this technique.

BRIEF DESCRIPTION OF THE DRAWINGS

The invention is explained in greater detail by way of an embodiment which is shown schematically in the drawings below.

DETAILED DESCRIPTION OF THE PREFERRED EMBODIMENTS

Figure 1:
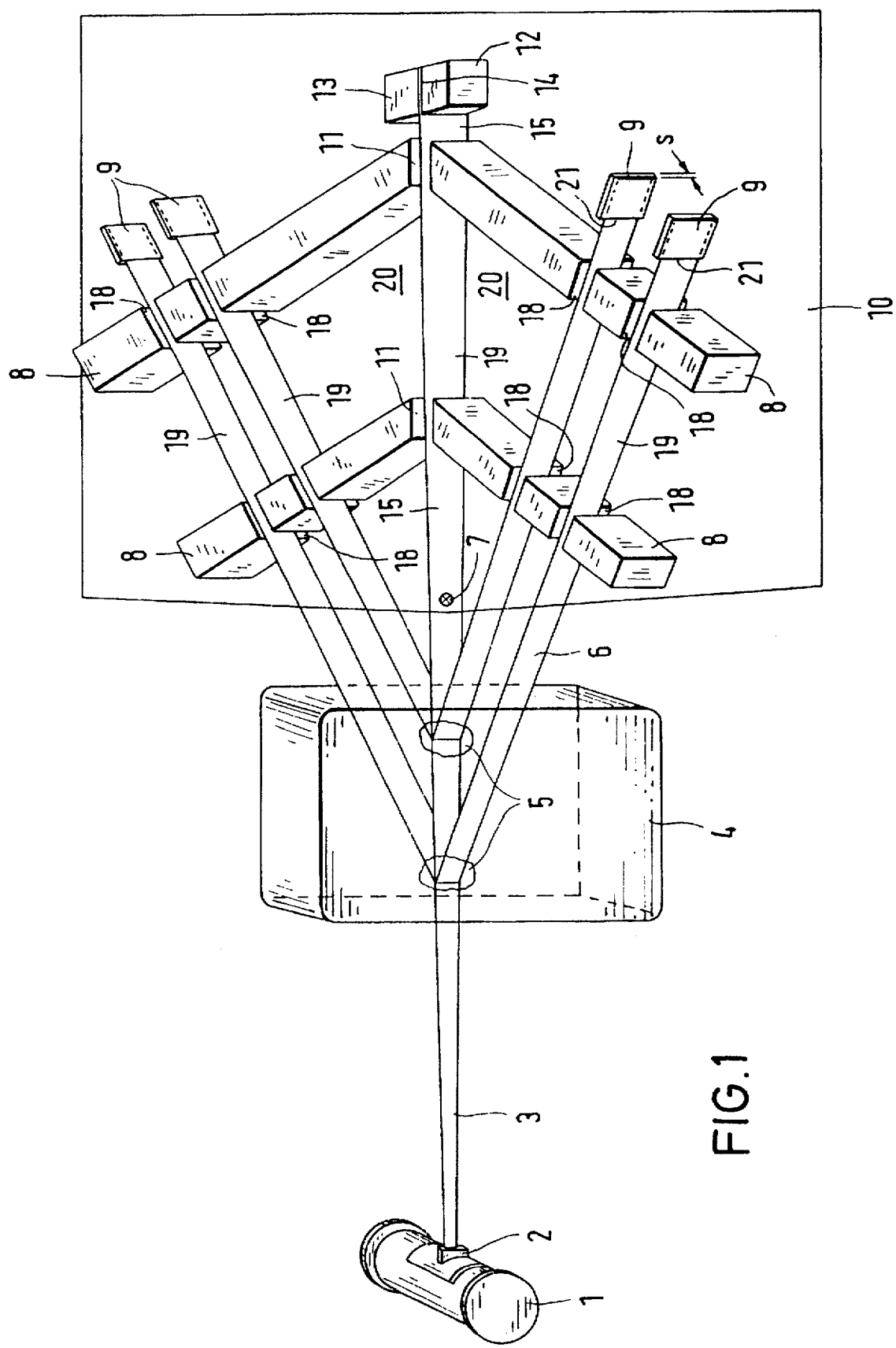
FIG. 1 shows a spatial representation of an arrangement for collimation and detection of diffracted, plane fan beams along an x-ray beam penetrating an object.
Figure 2:
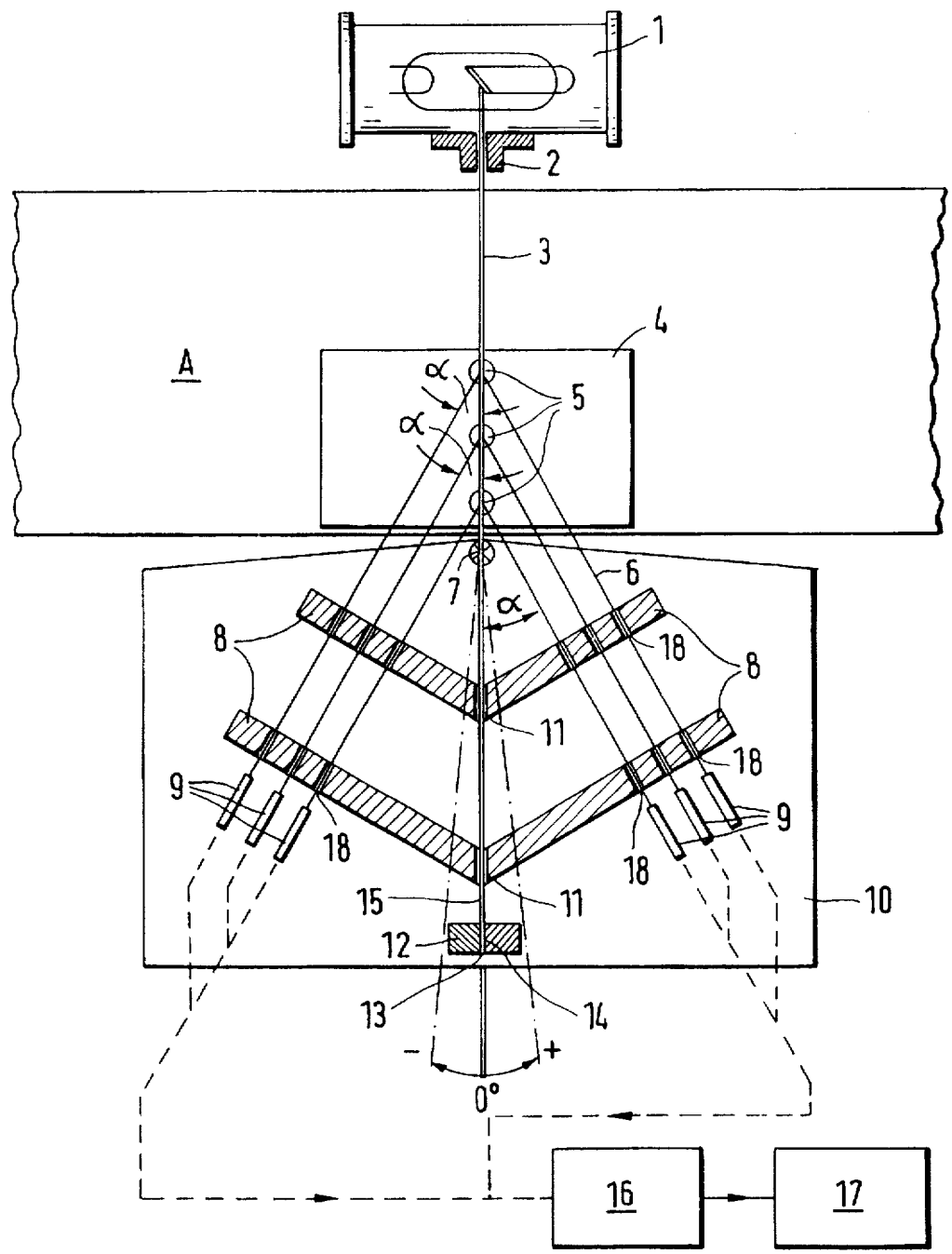
FIG. 2 is a plan view of the arrangement for collimation and detection illustrated in FIG. 1 with additional signal processing circuitry shown in block circuit diagram.

Referring to FIGS. 1 and 2, there is shown an x-ray source 1 (x-ray generator) which collimates x-ray radiation smaller than 100 KeV, for example, by means of a diaphragm 2, to create an incident x-ray fan beam 3 having a small cross section of less than 1 mm thickness and approximately 10 mm in height. X-ray fan beam 3 exiting diaphragm 2 has a polychromatic energy distribution and penetrates an object 4 in an examination region A for identifying crystalline and polycrystalline materials at predetermined locations, or subregions, at which diffraction centers 5 are generated along the x-ray. The portion of the incident x-ray fan beam 3 transmitted straight through object 4 is designated with reference numeral 15. On the opposite side of examination region A from x-ray source 1, collimators 8 are disposed having slot-shaped collimating windows 18 arranged symmetrically around the axis of central x-ray 3, 15 in a plane 20 extending perpendicularly to the fan plane 19 of x-ray fan beam 3, 15. Collimators 8 may be arranged in a single row or behind one another in a multi-row construction, with the collimating windows 18 extending parallel to one another on the respective sides of the axis of central x-ray fan beam 3, 15, which windows are respectively arranged at a fixed angle α to the axis of central x-ray fan beam 3, 15. At the respective collimating windows 18 of the rear collimators 8, detectors 9 are arranged in the respective planes 19 of the fan beams 6 collimated by collimating windows 18, which detectors capture the radiation of x-ray fan beams 6 diffracted by diffraction centers 5.

Detectors 9 capture the energy spectra of the diffracted radiation and forward them to a data processing arrangement 16 in which the data are converted into usable signals and can be displayed in an adjoining output unit 17. Furthermore, an automatic evaluation of the examination is possible by comparing the measured spectra to known spectra of explosive substances that are stored in the system.

Deviating from the representations of FIGS. 1 and 2, collimating windows 18 may be arranged in a plurality in parallel next to one another on the collimators 8 at a respectively constant angle α within an angular region between 2.4° and 3° with respect to the axis of central x-ray fan beam 15.

Collimating windows 18 of collimators 8 have a width of ≦1 mm, preferably in the range between about 0.3°–0.5° mm, and a height of approximately 10 mm. Silicon photodetectors 9, for example, are arranged at collimating windows 18, with the photodetectors having an end face having an area of about 1 mm² to 5 mm² to receive the diffracted, collimated fan beam 6. Since the thickness of the collimated beam bundle, preferably at the detector, is in the range between about 0.3 to 0.5 mm for reasons of attaining a high energy resolution, it becomes possible to use a silicon photodiode 9 as a semiconductor detector. In x-ray technology, silicon photodiodes are generally used as detectors for α and β radiation. This is done, in particular, because the radiation-sensitive charging zone within the semiconductor material has a thickness of approximately 0.3 mm. According to its ordinal number, silicon is in a position to completely absorb α and β radiation within this material thickness. This is the case to a much lesser extent with high energetic γ radiation between 10 and 100 KeV. Therefore, the silicon photodiode 9 is employed such that the collimated fan beam 6 is incident parallel or longitudinal to the semiconductor-sensitive zone or plane. Since the thickness of the fan beam and the sensitive semiconductor zone are within the same magnitude, a relevant loss of information does not here occur. Furthermore, it is advantageous that the thin detector zone offers an additional collimation because radiation which passes the detection plane laterally must, by its nature, come from a solid angle which is not to be considered.

The known drawbacks of silicon material which are due to its small photoabsorption in the energy range of larger than 50 KeV can be mitigated by connecting several detectors in parallel. Sine the energy range of smaller than 20 KeV is not of interest for obtaining the diffraction spectra, the Compton edge does not have any negative effects on the evaluation.

The subregions having diffraction centers 5 formed in the depth of the examination object along the incident x-ray fan beam 3 may also be examined in the manner described above in further planes, for example, in an inclined or perpendicular plane. In such a case, diaphragm 2 at x-ray source 1 would be supplemented by a further perpendicular or inclined diaphragm and the collimation and detection arrangement would be supplemented by further collimators and detectors in these planes in a manner which is not shown.

The collimation and detection arrangement offers the further advantage of a compact construction, which makes it possible to adjust the entire system in a simple manner. It is obvious that the adjustment has a decisive influence on the selectivity and thus on the recognizability of the material and the detection probability. A one-time adjustment of such a system, for example, during its assembly, is not sufficient. On the contrary, it must be assumed that an automatic readjustment must take place at regular intervals, for example, prior to every measurement of an examination object.

Figure 3:
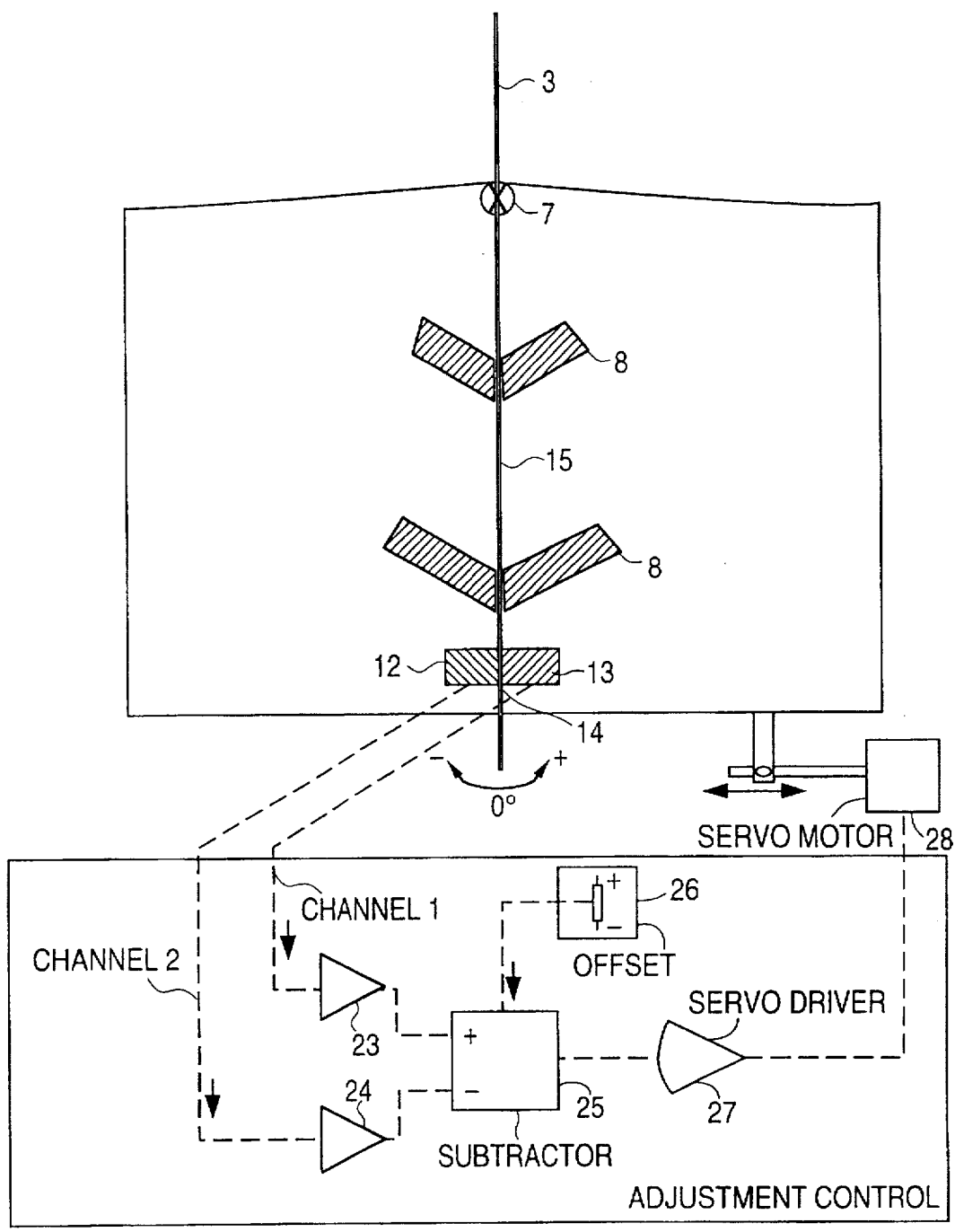
FIG. 3 is a partial section of the collimation arrangement with a representation of means used for orientation and adjustment.

For these reasons, the above-described arrangement is additionally provided with a corresponding adjustment arrangement and therefore the collimator and detector arrangement 8, 9 is arranged on a joint support unit 10 and comprises a central collimator 11 which can be oriented toward the focus of x-ray source 1 via a front bearing point 7 for automatic orientation and adjustment of collimators 8 and detectors 9. Referring additionally to FIG. 3, central collimator 11 is comprised of individual detectors 12, 13 which are arranged in a pair opposite of one another at their contact surfaces 14 and which are decoupled in terms of their signals, which is carried out by a thin light barrier (not shown) between the two detectors.

The two detectors 12, 13 are hit in their adjusted state by central ray 15 with equal intensity. This results in output signals of identical amplitude which are amplified by amplifiers 23 and 24 and supplied to a subtractor 25, which may receive an offset voltage from an offset potentiometer 26 for initially adjusting subtractor 25 when the system is put into service. If the amplified signals input to subtractor 25 are identical in amplitude, the output is "0", i.e., an error signal is not forwarded to the servodriver 27, and servomotor 28 remains at rest.

If the system is maladjusted, however, one of the two detectors 12, 13 is irradiated more intensively than the other detector. Corresponding to the direction of the maladjustment, a positive or negative output signal is generated at the output of the subtractor 25 which is forwarded to servodriver 27 for causing servomotor 28 to shift the entire collimating unit until the two detectors are again irradiated with the same intensity.

Automatic adjustment takes place such that, if the detection unit is oriented precisely, central beam 15 emitted by x-ray source 1 penetrates central collimator 11 and preferably identical signal components are generated in each individual detector 12, 13. In the event of a faulty adjustment, automatic readjustment can take place by an adjustment device, (see adjustment control), via the evaluation of the detection signals. The adjustment of a second plane takes place in the same manner, for example, with a second detector pair which is offset by 90°.

The individual detectors 12, 13, also referred to as a split detector, may be comprised of 2 scintillation detectors if the adjustment of the arrangement takes place in one plane or of four detectors if the adjustment of the arrangement takes place, for example, in both horizontal and vertical planes.

Figure 4:
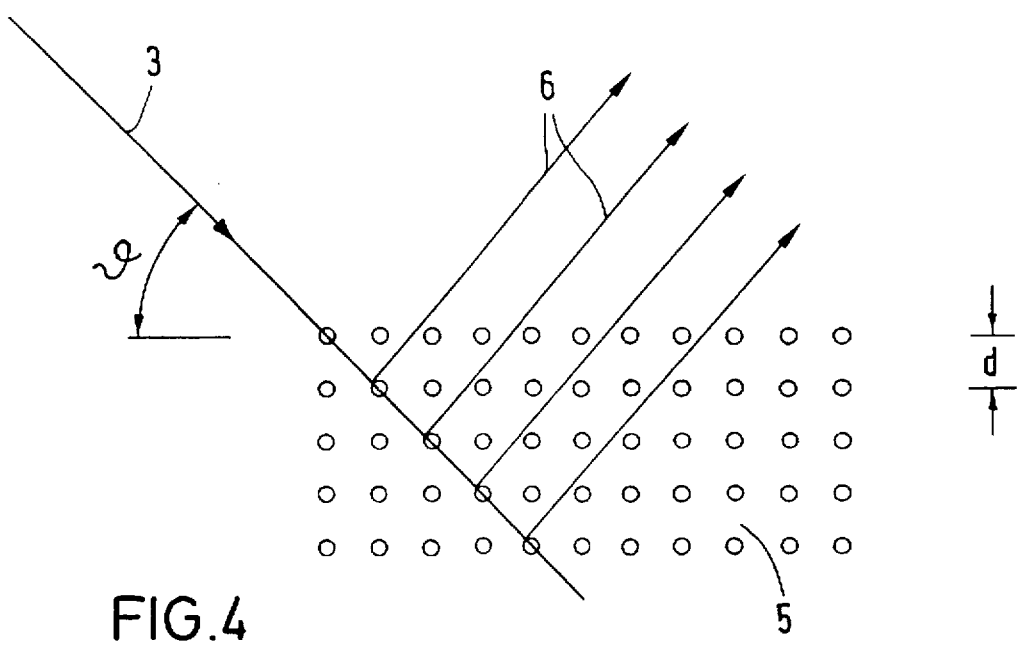
FIG. 4 is a schematic representing the physical effect of the diffraction of x-rays at lattice planes of crystalline and polycrystalline materials.

FIG. 4 shows the principle of the physical effect of diffraction, for example, of a material with a crystalline or polycrystalline lattice structure which is penetrated by an x-ray fan beam having a small cross section. In the example shown here, x-ray fan beam 3 penetrates the crystal planes separated from one another at a material-specific spacing d, with the individual quanta being diffracted at this structure.

Figure 5:
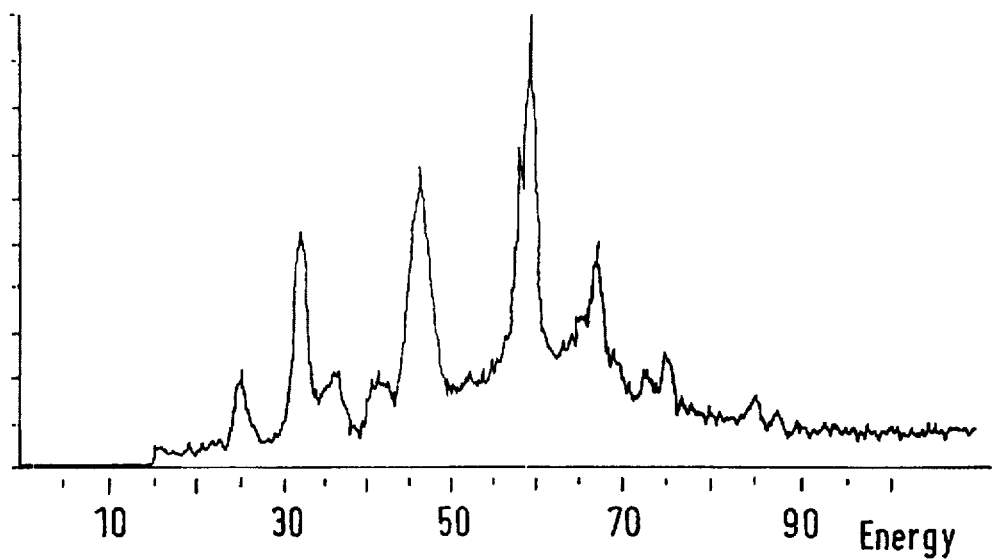
FIG. 5 is a graph showing energy spectra representing a polycrystalline structure of an explosive substance.

FIG. 5 shows a graph of characteristic energy maxima obtained in accordance with the above-described method, as they are generated, for example, by explosive substances due to their polycrystalline structure.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A method for identifying crystalline and polycrystalline material in an object, comprising:

placing the object in an examination region;

passing x-rays having a polychromatic energy distribution through a diaphragm to create a central x-ray beam in a fan plane that is projected into the examination region for irradiating a cross section of the object, the x-rays being diffracted by individual subregions of the object along the cross section in dependence of the presence of at least one of crystalline and polycrystalline material in a respective one of the individual subregions;

arranging collimators with collimating windows beyond the examination region with respect to the diaphragm, each collimating window covering a fixed, predetermined subregion of the examination region and extracting at least one diffracted plane fan beam from the respective individual subregion of the object;

providing a detector comprising a silicon photodiode including an end face having an area of 1 $mm^2$ to 5 $mm^2$ behind a respective one of the collimating windows so that each diffracted x-ray plane fan beam exiting a respective one of the collimating windows is incident on a respective one of the end faces of the silicon photodiodes; and capturing energy spectra of the diffracted x-ray plane fan beam exiting a respective one of the collimating windows with a respective one of the silicon photodiodes for converting the captured energy spectra into signals usable in a data processing arrangement.

2. The method according to claim 1, wherein the arranging step includes arranging the collimators in a plane which is perpendicular to the fan plane of the central x-ray fan beam for extracting a predetermined number of diffracted, plane fan beams which are incident symmetrically around the axis of the central x-ray fan beam.

3. The method according to claim 1, wherein the arranging step includes arranging the collimators in parallel behind one another, wherein the diffracted fan beams penetrate collimating windows disposed in parallel in the parallel arranged collimators.

4. The method according to claim 1, wherein the arranging step includes arranging the collimators so that each diffracted beam fan penetrates collimating windows of collimators arranged in parallel behind one another.

5. The method according to claim 1, wherein the arranging step includes arranging the collimators with collimating windows that form x-ray fan beams each having a cross section of with a width of $\leq 1$ mm.

6. The method according to claim 1, wherein the width of the cross section of each x-ray fan beam is in a range between about 0.3 to about 0.5 mm, and the cross section has a height of $\leq 10$ mm.

7. The method according to claim 1, wherein the arranging step includes arranging the collimators so that the collimating windows are at a predetermined fixed angle $\alpha$ in an angular region between about 2° and 4° with respect to the axis of the central x-ray fan beam.

8. The method according to claim 7, wherein the angle $\alpha$ is between about 2.4° and 3°.

9. The method according to claim 1, wherein the capturing step includes providing the respective silicon photoconductors so that each diffracted fan beam is incident into a plane of a sensitive semiconductor layer of the silicon photodetectors.

10. The method according to claim 9, wherein the thickness of the sensitive semiconductor layer operates to additionally collimate a respective one of the diffracted fan beams.

11. An arrangement for identifying crystalline and polycrystalline material in an object, comprising:

an x-ray source including a diaphragm for projecting a central x-ray beam having a polychromatic energy distribution in a fan plane into an examination region containing the object for irradiating a cross section of the object, the x-rays being diffracted by individual subregions of the object along the cross section in dependence of the presence of at least one of crystalline and polycrystalline material in a respective one of the individual subregions;

collimators arranged beyond the examination region relative to the x-ray source, the collimators being arranged in at least one row symmetrically around the axis of the central x-ray beam in a plane extending perpendicularly to the fan plane of the central x-ray beam and including collimating windows extending in parallel with respect to one another and respectively at a fixed angle $\alpha$ with respect to the axis of the central x-ray beam, each collimating window covering a fixed, predetermined subregion of the examination region and extracting at least one diffracted plane fan beam from the respective individual subregion of the object; and detectors each arranged at a respective one of the collimating windows of the collimators in the plane of the respectively collimated fan beam for capturing energy spectra of the diffracted x-ray plane fan beam exiting a respective one of the collimating windows and converting the energy spectra into signals for subsequent use in a data processing arrangement, wherein the detectors each comprises a silicon photodiode including an end face having an area of 1 mm$^2$ to 5 mm$^2$ behind a respective one of the collimating windows so that each diffracted x-ray plane fan beam exiting a respective one of the collimating windows is incident on a respective one of the end faces of the silicon photodiodes.

12. The arrangement according to claim 11, further comprising a support unit on which the collimators are arranged and a central collimator oriented toward a focus of the x-ray source for automatic orientation and adjustment of the detectors.

13. The arrangement according to claim 11, wherein the central collimator includes a pair of detectors for adjustment and orientation of the other collimators, the pair of detectors being decoupled in terms of their signals.

14. The arrangement according to claim 11, wherein the at least one row of collimators includes multiple rows of collimators arranged one behind another.

15. The arrangement according to claim 11, wherein the fixed angle of inclination $\alpha$ of the collimating windows of the collimators lies in a range between about 2.4° to about 3°.

16. The arrangement according to claim 11, wherein the collimating windows of the collimators have a width of $\leq 1$ mm, and a height of $\leq 10$ mm.

17. The arrangement according to claim 16, wherein the width of the collimating windows is in a range between about 0.3 mm to about 0.5 mm.

* * * * *